US010119920B2

(12) United States Patent
Mizutani et al.

(10) Patent No.: US 10,119,920 B2
(45) Date of Patent: Nov. 6, 2018

(54) METHOD COMPRISING EVALUATING SUBSTRATE BY POLARIZED PARALLEL LIGHT

(71) Applicants: Vision Psytec Co., Ltd., Nagano (JP); Mipox Corporation, Tokyo (JP); National Institute of Advanced Industrial Science and Technology, Tokyo (JP); Fuji Electric Co., Ltd., Kanagawa (JP)

(72) Inventors: Seiji Mizutani, Nagano (JP); Kenji Nakagawa, Tokyo (JP); Tomohisa Kato, Ibaraki (JP); Kensuke Takenaka, Kanagawa (JP)

(73) Assignees: Fuji Electric Co., Ltd., Kanagwa (JP); Mipox Corporation, Tokyo (JP)

( * ) Notice: Subject to any disclaimer, the term of this patent is extended or adjusted under 35 U.S.C. 154(b) by 0 days.

(21) Appl. No.: 15/867,345

(22) Filed: Jan. 10, 2018

(65) Prior Publication Data

US 2018/0195952 A1    Jul. 12, 2018

Related U.S. Application Data

(63) Continuation of application No. PCT/JP2016/082770, filed on Nov. 4, 2016.

(51) Int. Cl.
*G01N 21/95* (2006.01)
*G02B 21/00* (2006.01)
(Continued)

(52) U.S. Cl.
CPC ......... *G01N 21/9501* (2013.01); *G01B 11/30* (2013.01); *G01N 21/21* (2013.01);
(Continued)

(58) Field of Classification Search
CPC ........ G01N 21/21; G01N 21/23; G01N 21/87; G01N 21/88; G01N 21/8803;
(Continued)

(56) References Cited

U.S. PATENT DOCUMENTS

| 5,333,052 A * | 7/1994 | Finarov | G01B 11/0641 |
| | | | 356/369 |
| 9,099,350 B2 | 8/2015 | Nakamura et al. | |
| 2015/0168311 A1* | 6/2015 | Seki | G01N 21/9501 |
| | | | 356/51 |

FOREIGN PATENT DOCUMENTS

| JP | 2011-220744 A | 11/2011 |
| JP | 2012-174896 A | 9/2012 |

(Continued)

OTHER PUBLICATIONS

International Search Report for PCT/JP2016/082770, dated Jan. 31, 2017, 2 pages.

*Primary Examiner* — Gordon J Stock, Jr.
(74) *Attorney, Agent, or Firm* — Blank Rome LLP

(57) ABSTRACT

There is provided a method that makes it possible to observe fine crystal defects using light of a visible region. The method includes illuminating a substrate with polarized parallel light and evaluating a crystal quality of at least a part of the substrate from an image obtained by light transmitted through or reflected by the substrate. The half width HW, the divergence angle DA, and the center wavelength CWL of the parallel light satisfy conditions given below $3 \leq HW \leq 100$ $0.1 \leq DA \leq 5$ $250 \leq CWL \leq 1600$ (Continued)

where the center wavelength CWL and the half width HW are expressed in units of nm and the divergence angle DA is expressed in units of mrad.

19 Claims, 5 Drawing Sheets

(51) Int. Cl.
  *G01N 21/892*    (2006.01)
  *G01B 11/30*    (2006.01)
  *G01N 21/21*    (2006.01)
  *G01N 21/88*    (2006.01)

(52) U.S. Cl.
  CPC ....... *G01N 21/8806* (2013.01); *G01N 21/892* (2013.01); *G02B 21/0004* (2013.01); *G02B 21/0092* (2013.01); *G01N 2021/8848* (2013.01); *G01N 2021/8925* (2013.01)

(58) Field of Classification Search
  CPC ........... G01N 21/8806; G01N 21/8914; G01N 21/892; G01N 21/8921; G01N 21/896; G01N 21/95; G01N 21/9501; G01N 21/9505; G01N 2021/8848; G01N 2021/8924; G01N 2021/8925; G01B 11/30; G01B 11/303; G01B 11/306; G01B 9/04; G02B 21/0004; G02B 21/0016; G02B 21/0092
  USPC .......... 382/145, 149; 356/30, 364, 365, 369, 356/370, 600, 601, 237.1, 249.1, 239.7, 356/237.2, 237.3, 237.4, 237.5
  See application file for complete search history.

(56) References Cited

FOREIGN PATENT DOCUMENTS

| | | |
|---|---|---|
| JP | 2012-247397 A | 12/2012 |
| JP | 2014-002104 A | 1/2014 |
| JP | 2014-189484 A | 10/2014 |
| JP | 2015-178438 A | 10/2015 |

\* cited by examiner

METHOD COMPRISING EVALUATING SUBSTRATE BY POLARIZED PARALLEL LIGHT

RELATED APPLICATIONS

The present application is a continuation of International Patent Application No. PCT/JP2016/082770 filed Nov. 4, 2016, which claims priority to Japanese Application No. 2015-218003 filed Nov. 5, 2015. The entire contents of those applications are hereby incorporated by reference.

TECHNICAL FIELD

The present invention relates to a method including evaluation of a substrate using polarized parallel light.

BACKGROUND ART

Japanese Laid-open Patent Publication No. 2015-178438 describes the provision of a gallium nitride freestanding substrate that has favorable crystallinity and is capable of forming high-quality semiconductor device structures. As gallium nitride crystals approach perfect crystals, an abnormal transmission phenomenon occurs where X rays pass through the crystals with no attenuation due to the absorption coefficient for X-rays being exhibited, so that by using this and using a transmitted X-ray topography as a test item, it is possible to detect unacceptable defects in the testing (inspection) process.

Japanese Laid-open Patent Publication No. 2014-189484 describes how it is difficult to form a high-quality epitaxial layer with extremely few crystal defects on a substrate due to crystal defects in the surface of an SiC monocrystalline substrate propagating to the epitaxial layer or due to disturbances in the crystal structure to the defect-free portions inside the substrate. The method for manufacturing a silicon carbide semiconductor substrate disclosed in this document includes: a defect position identifying step that identifies positions of crystal defects formed in a silicon carbide semiconductor substrate by X-ray topography or photoluminescence; a crystal defect nullifying step that performs a nullifying process which suppresses propagation of crystal defects to the epitaxial layer by irradiating the identified regions of the crystal defects with a particle beam; and an epitaxial layer forming step that forms an epitaxial layer on the substrate that has been subjected to the nullifying process.

Japanese Laid-open Patent Publication No. 2014-2104 discloses the provision of a method of evaluating a SiC monocrystalline substrate that can evaluate the dislocation density of the SiC monocrystalline substrate via reflection X-ray topography without using a monochromator. The method of evaluating an SiC monocrystalline substrate in this document evaluates dislocation in the SiC monocrystalline substrate using reflection X-ray topography and is characterized by obtaining an X-ray topography image of the SiC monocrystalline substrate using MoKα rays as the X-ray source and an asymmetric reflective surface as the diffraction surface, and by measuring the dislocation density of the SiC monocrystalline substrate using the X-ray topography image.

SUMMARY OF INVENTION

To evaluate crystal defects in an SiC monocrystalline substrate, a GaN monocrystalline substrate, or the like, X-ray topography method and/or photoluminescence method are conventionally used. To test or observe a substrate using X-ray topography method or photoluminescence method, special equipment such as an X-ray generator and cooling equipment are necessary, so that these methods cannot be said to be economical. If it were possible to perform the same or similar tests or observations as these methods using light in the visible region, the ultraviolet region, or the infrared region, this would be economical, leading to more widespread applications.

One aspect of the present invention is a method including the following steps.
1. Illuminating a substrate with polarized parallel light.
2. Evaluating a crystal quality of at least a part of the substrate from an image obtained by light transmitted through or reflected by the substrate.

Here, a center wavelength CWL, a half width HW, and a divergence angle DA of the parallel light satisfy conditions given below.

$$3 \leq HW \leq 100 \tag{1}$$

$$0.1 \leq DA \leq 5 \tag{2}$$

$$250 \leq CWL \leq 1600 \tag{3}$$

The center wavelength CWL and the half width HW are expressed in units of nm and the divergence angle DA is expressed in units of mrad.

The inventors of the present application revealed that with parallel light that satisfies Conditions (1) and (2) described above, it is possible to non-destructively evaluate the crystal quality, as examples, defects due to crystal quality, distortions due to crystal defects, lattice distortions due to dislocations in an atomic arrangement, and the like of at least part of a substrate by observing the substrate using light with a center wavelength in the region in Condition (3), that is, the visible light region or a region close to visible light.

The step of evaluating may include evaluation using a crossed Nicol method and in this case, it is desirable for the extinction ratio ER of the polarizer and the analyzer that face one another with the substrate in between to satisfy a condition below.

$$10^{-4} < ER < 10^{-2} \tag{4}$$

The step of evaluating may include varying the depth of focus. It is also desirable for the evaluating to include evaluating lattice distortions based on or due to displacements in an atomic arrangement. It is also possible to evaluate photoelasticity. The lattice distortions due to displacements in an atomic arrangement may include threading screw dislocations, threading edge dislocations, basal plane dislocations, stacking faults, inclusions, and processing damages (machining damages). Note that processing damages may include a processing-affected layer, latent flaws, or other damages.

This method may include manufacturing a product that uses a substrate selected by the evaluating, and may be a method of manufacturing a product that uses the substrate. The method may also include subjecting a region of the substrate determined by the evaluating to a treatment (processing).

The substrate illuminated or radiated with parallel light may include semiconductor substrates, semiconductor monocrystalline substrates and substrates produced by epitaxial growth on the same, mineral substrates, glass substrates, plastic substrates, and plastic film substrates. The silicon semiconductor substrates may include uniaxially polarized crystalline substrates including such as monocrystalline 4H—SiC substrates and monocrystalline 6H—SiC substrates; wide bandgap semiconductor substrates including such as at least one of monocrystalline GaN, monocrystalline $Ga_2O_3$, and monocrystalline AN; transparent oxide monocrystalline substrates such as monocrystalline diamond and monocrystalline sapphire; monocrystalline silicon substrates; and monocrystalline silicon epitaxial substrates. Polycrystalline silicon substrates can be given as an example of semiconductor substrates.

DESCRIPTION OF EMBODIMENTS

Figure 1:
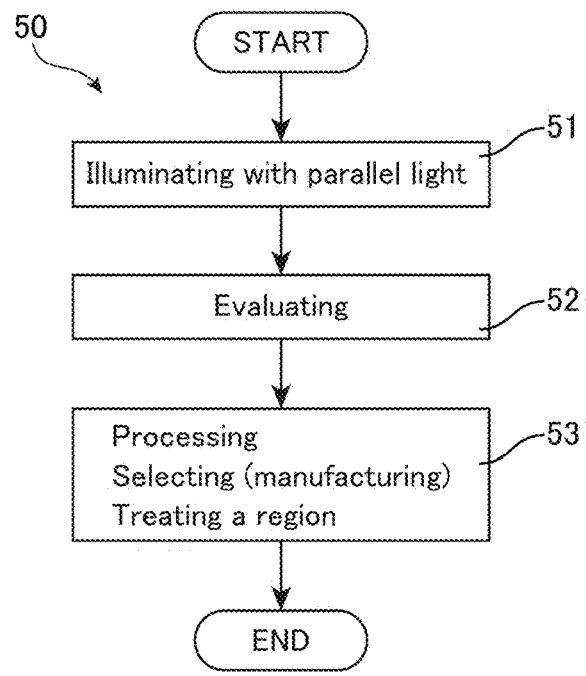
FIG. 1 is a flowchart depicting a method, for example, a manufacturing method, including a step of evaluating a substrate using an image acquired by parallel light.

A method of observing the crystal quality of a substrate and/or a phenomenon that derives from the crystal quality with an optical microscope that uses light of specified conditions and/or non-destructively testing and evaluating based on the optical microscope image is described further below. The examples of crystal quality are crystal dislocations, such as threading screw dislocations, threading edge dislocations, basal plane dislocations, and stacking faults; inclusions; processing damages (machining damages); other lattice distortions due to some kinds of displacement in an atomic arrangement; and photoelasticity in some kinds of material or substrate, in particular a uniaxially polarized crystalline substrate, such as a monocrystalline 4H—SiC substrate but not limited to.

Conventionally, synchrotron radiation X-ray topography is the main method used to non-destructively evaluate crystal dislocations, such as threading screw dislocation, threading edge dislocation, and basal plane dislocation, and lattice distortions, such as stacking faults and processing damage in a uniaxially polarized crystalline substrate, such as a monocrystalline 4H—SiC substrate or a monocrystalline 6H—SiC substrate. This is also the case for evaluation of crystal dislocation defects in various crystalline materials, including other semiconductors. The resolution of synchrotron radiation X-ray topography is limited by the two-dimensional detector (such as a nuclear dry plate) and is around 1 μm. This resolution depends on the particle diameter of fine grains of the photosensitive material (emulsifier), such as silver halide or the like that is coated on the nuclear dry plate or the like used as the two-dimensional detector. Accordingly, what is observed in a synchrotron radiation X-ray topography image is distortions in X-ray diffraction due to elastic strain produced by crystal dislocations.

However, to perform synchrotron radiation X-ray topography, a large synchrotron radiation facility is needed to produce a source for the synchrotron radiation. This results in the problem that a large facility cost and maintenance costs are required, and the usage time is also limited. There is also the problem that warping of the substrate has a large influence on the result and it is difficult to observe the whole area with the same contrast.

From this viewpoint, development is ongoing into laboratory-scale X-ray topography equipment that uses a small X-ray source. However, since X-rays are still used, the problem of the testing apparatus being costly remains as before. There are additional real-world equipment-related problems in that it is necessary to notify central government agencies, public organizations, private agencies, and the like and to appoint an authorized or licensed chief X-ray inspection engineer.

For semiconductor substrates such as monocrystalline 4H—SiC substrates, development is also ongoing into a method of evaluating crystal dislocations using photoluminescence. However, there is the problem that testing using photoluminescence is limited to materials and types of defect where light is emitted by photoexcitation.

On the other hand, when crystal dislocations are present, a phenomenon called birefringence occurs. While the refractive index is a numerical value expressing the ease with which light can advance, birefringence is a state where the refractive index for differently polarized light changes or not stable within a material. When observing a substance in which birefringence has occurred with a polarizing microscope, phase disturbances due to phase differences (so-called "retardation") are observed as optical distortion. As one example, since micropipe defects present in a monocrystalline 6H—SiC substrate are a type of threading screw dislocation, birefringence will occur and it is known that when such micropipes are observed with a polarizing microscope, optical distortion caused by interference patterns will be observed.

However, conventional polarizing microscopes are limited to observation of crystal defects, such as micropipe defects, with relatively large optical distortion, so that it has not been possible to observe and photograph slight retardation based on crystal dislocations, such as threading screw dislocation, penetrating edge dislocation, and basal plane dislocation where displacement of the atomic arrangement occurs at the atomic level.

FIG. 1 depicts, by way of a flowchart, an overview of a method including a step of evaluating a substrate using parallel light. This method 50 has a step 51 of illuminating a substrate with polarized parallel light and a step 52 of evaluating crystal quality (as examples, defects due to crystal quality, distortion due to crystal defects, and lattice distortions due to displacement in the atomic arrangement) of at least a part of the substrate by way of an image produced by light transmitted through or reflected by the substrate. In addition, in a step 53, the substrate is processed or treated as necessary. The step 53 may be a step for manufacturing a product that uses a substrate selected by the evaluation in the step 52, may be a step for performing some processes or treatments on a region of the substrate decided by evaluation, and may be a step for performing other kinds of processes based on the evaluation. Accordingly the method 50 may be a manufacturing method. Alternatively, the method 50 may be an evaluation method that performs evaluation only.

Figure 2:
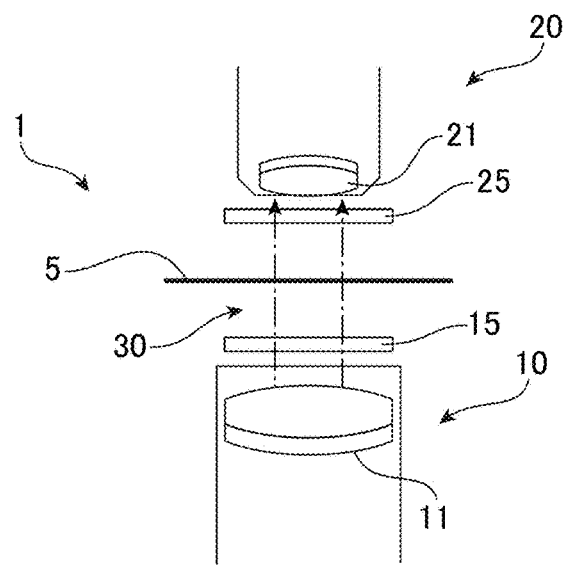
FIG. 2 depicts one example of an optical system that illuminates a substrate with parallel light.

FIG. 2 depicts an overview of an apparatus that acquires an image by illuminating or irradiating a substrate 5 to be observed with parallel light 30. This apparatus 1 (an optical system of a polarizing microscope) includes an illumination optical system (or light projecting optical system) 10 and a light receiving optical system (or imaging optical system) 20. The illumination optical system 10 outputs collimated light 30 through a telecentric condenser lens 11, and irradiates the collimated light (parallel light) 30 via a polarizer 15 onto the observation target 5, such as a substrate, that is being tested. In the light receiving optical system 20, light that has passed through the observation target 5, such as a substrate, is collected by an objective lens 21 after passing through an analyzer 25, the transmitted polarized light is detected by an image sensor (not illustrated), and a two-dimensional distribution of optical distortion (birefringence) of the observation target 5, such as a substrate, is acquired as video or an image from intensity information of the image sensor.

The conditions of the collimated light 30 are as follows.

$$3 \leq HW \leq 100 \tag{1}$$

$$0.1 \leq DA \leq 5 \tag{2}$$

$$250 \leq CWL \leq 1600 \tag{3}$$

Here, "CWL" is the center wavelength of the parallel light (in nm), "HW" is the half width (in nm), and "DA" is the divergence angle (in mrad). The extinction ratio ER of the polarizer 15 and the analyzer 25 is as follows.

$$10^{-4} < ER < 10^{-2} \tag{4}$$

The lower limit of condition (1) should preferably be over 3 and the upper limit should preferably be below 60. The lower limit of condition (2) should preferably be over 0.1 and the upper limit should preferably be below 3. One example of the center wavelength CWL satisfies the condition (3-1) below.

$$300 < CWL < 500 \tag{3-1}$$

Parallel light with the above conditions including condition (3-1) is one example of a preferable condition when evaluating an observation target whose bandgap is wider than 2.48 eV. This condition is suitable for, as one example case, observing optical distortion caused by crystal structure defects of a uniaxially polarized crystalline substrate such as a monocrystalline 4H—SiC substrate or a monocrystalline 6H—SiC substrate. The lower limit of condition (3-1) should preferably be 310 or higher and the upper limit should preferably be 460 or lower.

Another example of the center wavelength CWL satisfies the condition (3-2) below.

$$1100 < CWL < 1600 \tag{3-2}$$

This is one example of a favorable condition for observing optical distortion due to crystal structure defects in a monocrystalline silicon substrate, a monocrystalline silicon substrate with epitaxial growth, and a polycrystalline silicon substrate. The lower limit of condition (3-2) should preferably be 1200 or higher and the upper limit should preferably be 1550 or lower.

One example of a substrate to be measured is a substrate whose surface has been ground or polished so as to have a predetermined thickness. The thickness t of the measured substrate should preferably satisfy condition (5) below.

$$50 \leq t \leq 800 \tag{5}$$

Here, the thickness t is expressed in units of $\mu m$.

The lower limit of condition (5) should preferably be 60 or higher and the upper limit should preferably be 400 or lower. Due to the increase in transmittance, it becomes easy to observe distortion and the like. One example of a measured object of this thickness is a semiconductor monocrystalline substrate, which includes uniaxially polarized crystalline substrates such as a monocrystalline 4H—SiC substrate and a monocrystalline 6H—SiC substrate. The measured object may be a monocrystalline silicon substrate for use as a solar cell, may be a monocrystalline silicon substrate for a power device such as an IGBT, and as one example the thickness t is adjusted so as to be 60 $\mu m$ or larger and 150 $\mu m$ or smaller.

It is preferable for the front surface (upper surface) and rear surface (bottom surface) of the substrate to be measured to be polished, and preferable for at least one of the surface roughness Ra1 of the front surface and the surface roughness Ra2 of the rear surface to satisfy conditions (6) and (7) below.

$$0.001 \leq Ra1 \leq 30 \tag{6}$$

$$0.001 \leq Ra2 \leq 30 \tag{7}$$

Here, the surface roughness Ra1 and Ra2 are expressed in units of nm. The upper limits of conditions (6) and (7) should preferably be 5 or below and even more preferably 1 or below.

The conditions (1) to (7) can be flexibly selected in the ranges described above according to the conditions of the substrate to be measured, for example, the optical characteristics, economic conditions required by measurement, and the sensitivity and precision demanded for evaluation. As one example, when measuring a substrate with a bandgap of 2.48 eV or below, one example of favorable conditions when a certain cost can be tolerated for the optical systems and preparing the substrates is given below. Parallel light of these conditions can be supplied for example by an XS-1 polarizing microscope provided by Vision Psytec Co., Ltd.

$$3 < HW < 60$$

$$0.1 < DA < 3$$

$$300 < CWL < 500$$

$$10^{-4} < ER < 10^{-2}$$

$$50 \leq t \leq 400$$

$$0.001 \leq Ra1 \leq 1$$

$$0.001 \leq Ra2 \leq 1$$

In step 52, it is possible to detect transmitted polarized light obtained using the parallel light 30 with the conditions described above using an image sensor and to obtain a two-dimensional distribution of optical distortion (birefringence) of the observation target 5, such as a substrate, as video or an image from the intensity information of the image sensor. It is also possible, by varying the focal position by changing the distance between the light receiving optical system 20 and the observed object 5, to change the contrast of the image and obtain information on optical distortion in the depth direction of a uniaxially polarized crystal substrate, for example.

In step 52, it is possible to make observations in the same way as when making orthoscopic observations with a polarizing microscope where the polarizer 15 and the analyzer 25 are orthogonally oriented in a crossed Nicols condition so that the linearly polarized lights pass through respectively. It is also possible, while maintaining the crossed Nicols condition, to rotate the polarizer 15 and the analyzer 25 on the same axis synchronously and perform evaluation that distinguishes between threading-type crystal dislocations and other crystal dislocations or some other kinds of lattice distortion.

Light that satisfies the conditions (1) and (3-1) is quasi-monochromatic light in the region of visible light to near ultraviolet light, with one example of a light source being a UV-LED. For parallel light that satisfies the conditions above has not so strong coherency, if the coherency is too strong like laser light, much speckle noise will occur, but since the light is substantially coherent, it is possible to retain some slight retardation from when the light passes through the observation target as information. In addition, since the diffusion angle (divergence angle) DA is highly parallel within the range of condition (2), by illuminating with such highly collimated light, it is possible to obtain an image in which even smaller retardation when the light passes through the observation target 5, such as lattice distortion based on displacement in the atomic arrangement, is kept as information.

The upper limit in Equation (3-1) is limited by the transmittance and the sensitivity to distortion of the parallel light 30, and while observation may be performed using a wavelength that exceeds condition (3-1), it becomes difficult in step 52 to evaluate lattice distortion due to or based on displacement of the atomic arrangement. The lower limit of Equation (3-1) is because the wavelength sensitivity of the CDD or CMOS that is the light receiving element suddenly drops at around 300 nm, which makes it difficult to provide a light receiving system with high sensitivity at low cost.

EXAMPLE 1

Figure 3A:
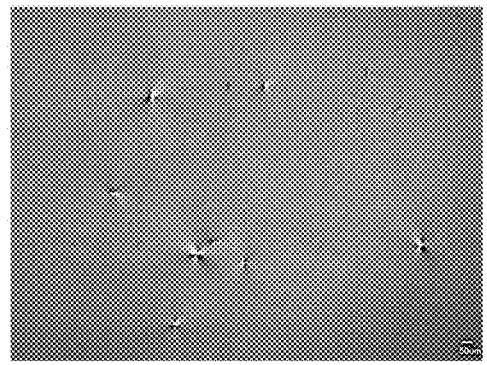
FIG. 3(a) is one example of imaging with an industrial microscope (white light) and FIG. 3(b) is one example of imaging using parallel light.
Figure 3B:
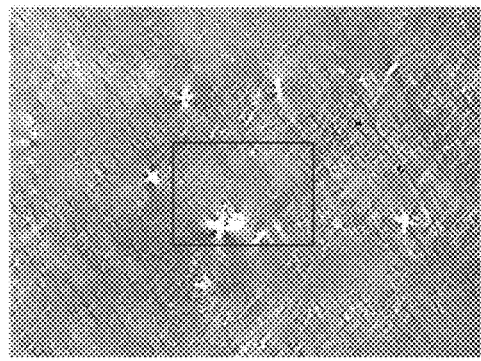

As the Example 1, an 8° off-axis p-type monocrystalline 4H—SiC substrate with a thickness of around 360 μm and a diameter of around 76.2 mm was evaluated. The results are shown in FIG. 3. FIG. 3(a) is the results when the surface of the substrate was observed using transmitted simple polarized light with an ECLIPSE LV100D industrial microscope made by Nikon, Inc., and FIG. 3(b) is the results when the same position is observed with a XS-1 polarizing microscope made by Vision Psytec, Co., Ltd. During these observations, the ECLIPSE LV100D industrial microscope used a white halogen lamp as the light source. For this reason, for the observations using the ECLIPSE LV100D industrial microscope, there is no concept of center wavelength CWL and half width HW. On the other hand, the XS-1 polarizing microscope uses a "UFLS-501-UV-UT-VI" UV-LED light source made by U-TECHNOLOGY Co., Ltd, the XS-1 polarizing microscope is set so as to illuminate (irradiate) the substrate with that the parallel light 30 that is composed of quasi-monochromatic light with a center wavelength CWL of 405 nm and a half width HW of 50 nm and has a divergence angle DA of 0.5 mrad or below, and acquired images using a combination of the polarizer 15 and the analyzer 25 where the extinction ratio ER is $10^{-3}$ or below.

Before observation, since the wafer to be observed had been subjected to Si face (preferential face) was finished with CMP (chemical mechanical polishing) and the C face (rear face) was mirrored, the C face side was changed to as the preferential face and finished with CMP by additionally polished with at set polishing depth of 10 μm. As a result, the surface roughness Ra1 and Ra2 (Ra) of both surfaces was estimated to be below 1 nm. After polishing, the p-type monocrystalline 4H—SiC substrate was ultrasonically washed in acetone and isopropyl alcohol, subjected to SPM (Sulfuric acid/hydrogen peroxide mixture) washing, and subjected to RCA washing (washing that is a combination of washing in an ammonia/hydrogen peroxide/water mixture called "SC1" or "APM" and washing in a hydrochloric acid/hydrogen peroxide/water mixture called "SC2" or "HPM") to sufficiently clean the surfaces.

When the substrate is a uniaxially polarized crystal substrate, the surface finishing of the substrate that is the observation target 5 should be at least mirrored and preferably have an equivalent smoothness to when CMP is used. Although it is preferable for substrates that are difficult to polish to have a surface roughness Ra1 and Ra2 of under 5 nm, a surface roughness of 5 nm or above is acceptable if observation is still possible.

Since matter adhering to the surfaces produces noise, it is preferable to make observations after performing washing according to various appropriate methods based on the material of the substrate. Although it is preferable for the warping ("SORT") of the substrate to be below 40 if it is not necessary to observe the entire face, warping of 40 or more is acceptable.

FIG. 3(a) is judged to be an image produced by transmitted simple polarized light when optical distortion of micropipe defects in the p-type monocrystalline 4H—SiC substrate as the observation target are observed. On the other hand, it can be understood that in FIG. 3(b), which is an image obtained when observing the same part using quasi-monochromatic parallel light with the XS-1 polarizing microscope made by Vision Psytec, Co., in addition to the micropipes, many optical distortions that cannot be observed with an industrial microscope are observed.

Figure 4A:
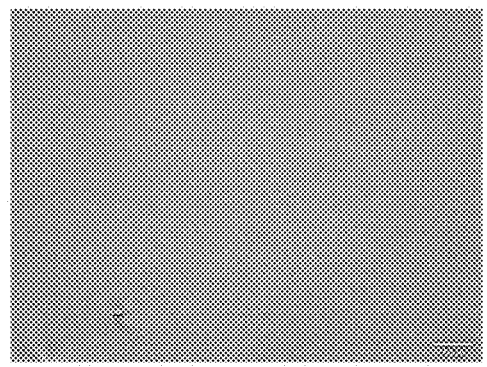
FIGS. 4(a) and (b) are images produced by enlarging parts of FIGS. 3(a) and (b) corresponding to a part indicated by a rectangle in FIG. 3(b).
Figure 4B:
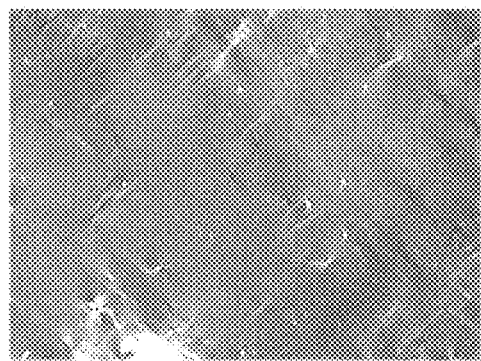

FIGS. 4(a) and 4(b) respectively correspond to FIGS. 3(a) and 3(b), and depict images produced by enlarging the parts indicated by the rectangle in FIG. 3(b) out of FIGS. 3(a) and 3(b). It can be understood that in the image (FIG. 4(b)) acquired by the polarizing microscope XS-1 made by Vision Psytec, Co., a large number of crystal dislocations, which cannot be detected with a normal industrial microscope, have been detected as optical distortions.

EXAMPLE 2

As the Example 2, a 4° off-axis n-type monocrystalline 4H—SiC substrate with a thickness of around 355 μm and a diameter of around 76.2 mm was evaluated. Before observation, the Si face on the preferential face side of the n-type monocrystalline 4H—SiC substrate was subjected to CMP with a target polishing amount of 1 μm and the C face on the rear surface was also subjected to CMP with a target polishing amount of 1 μm so that both surfaces were CMP polished. The surface roughness Ra1 and Ra2 (Ra) of both surfaces was estimated to be below 1 nm. After polishing, the n-type monocrystalline 4H—SiC substrate was ultrasonically washed in acetone and isopropyl alcohol, and subjected to SPM washing and then RCA washing to sufficiently clean the surfaces.

FIG. 5(a) is a photograph of transmitted polarized light taken by observing a substrate subjected to the treatment (processing) described above with an XS-1 polarizing microscope made by Vision Psytec, Co., Ltd. The conditions of the parallel light 30 are the same as in the Example 1. It should be noted that although the lower left region is white and difficult to evaluate due to an abnormal increase in the luminance of the image due to the influence of laser marks used to mark the substrate, this phenomenon does not occur if there are no distortions due to extreme unevenness produced by laser marking.

FIG. 5(b) depicts a transmitted X-ray topographic image produced by imaging of the same substrate using a laboratory-class compact X-ray topography apparatus. An Mo-ray source was used as the X-ray source, and the X-ray diffraction condition was set at [11-20] (φ=0°).

Figure 5:
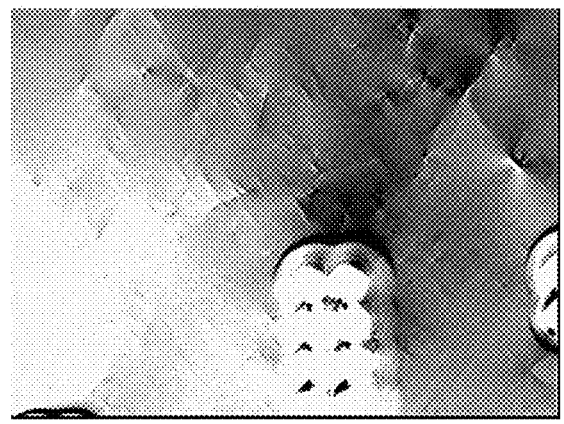
FIG. 5(a) is a different example of an image acquired by illuminating a substrate with parallel light.
FIG. 5(b) is a transmission X-ray topographic image of the same substrate.
FIG. 5(c) is a synchrotron radiation reflected X-ray topography image of the same substrate.
Figure 5:
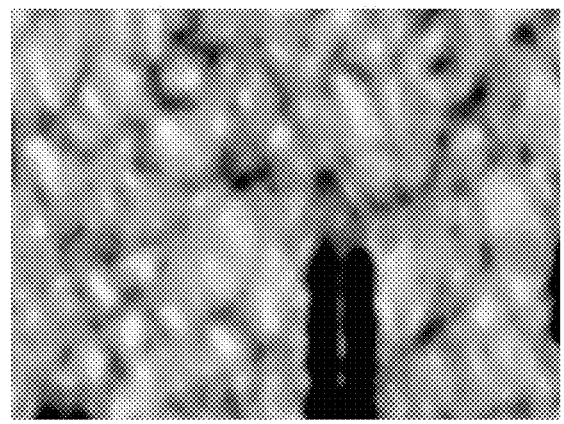
Figure 5:
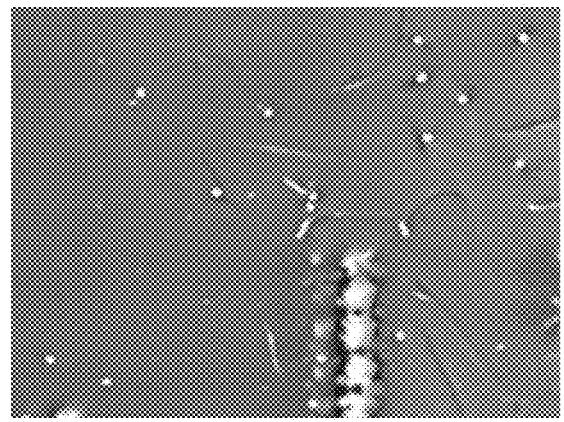

By comparing FIGS. 5(a) and 5(b), it is possible to see that the optical distortions observed in the transmissive polarized image of the XS-1 made by Vision Psytec, Co., Ltd. depicted in FIG. 5 (a) correspond to the black spots, that is, threading-type crystal dislocations, in the transmitted X-ray topography image depicted in FIG. 5(b).

FIG. 5(c) depicts a synchrotron radiation reflected X-ray topography image observed on the C face side of the same substrate. The wavelength of the X-rays is 0.15 nm, the diffraction plane of the X-ray beam is [11-2-8], and a nuclear dry plate was used as the two-dimensional detector.

By comparing FIGS. 5(a) and (c), it is confirmable that although distortions in X-ray diffraction in only the vicinity of the surface are observed in the reflected X-ray topography image, in the image of the transmitted polarized light produced by the XS-1 apparatus made by Vision Psytec, Co., Ltd., a larger number of optical distortions could be observed. Also, for the six threading screw dislocations observed in the upper right of FIG. 5(c), the optical distortions with substantially matching positions were observed in FIG. 5(a). It is therefore believed that the XS-1 apparatus made by Vision Psytec, Co., Ltd., is capable of observing threading screw dislocations using the image of transmitted polarized light.

EXAMPLE 3

As the Example 3, a 4° off-axis n-type monocrystalline 4H—SiC substrate with a thickness of around 351 μm and a diameter of around 76.2 mm was evaluated. The Si face on the preferential face side of this n-type monocrystalline 4H—SiC substrate was polished to CMP finish with a total target polishing amount of 125 μm and the C face on the rear surface was also polished with a target polishing amount of 125 μm to produce a single-sided CMP substrate with a residual thickness of around 100 μm. After polishing, the n-type monocrystalline 4H—SiC substrate was ultrasonically washed in acetone and isopropyl alcohol, and subjected to HF etching and SC-1 washing to sufficiently clean the surfaces.

Figure 6:
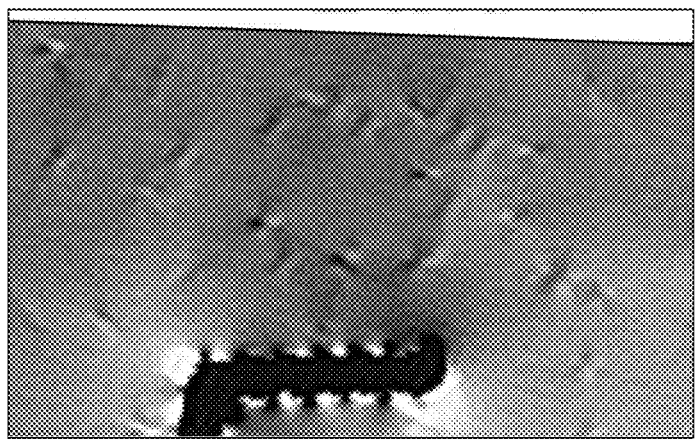
FIG. 6(a) is a different example of an image acquired by illuminating a substrate with parallel light.
FIG. 6(b) is an image that has been sharpened by image processing.
FIG. 6(c) is an image of etch pits.
Figure 6:
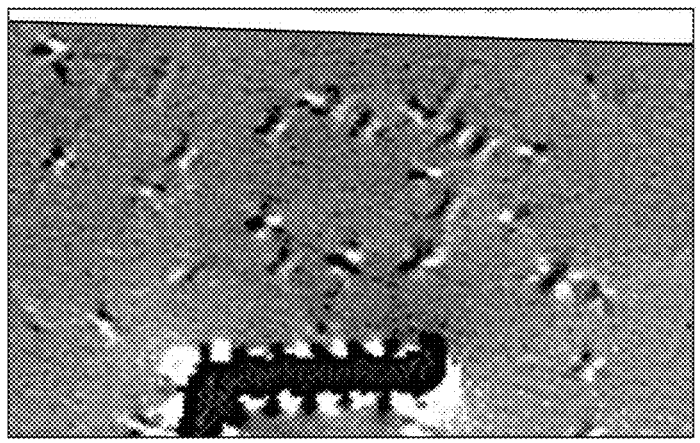
Figure 6:
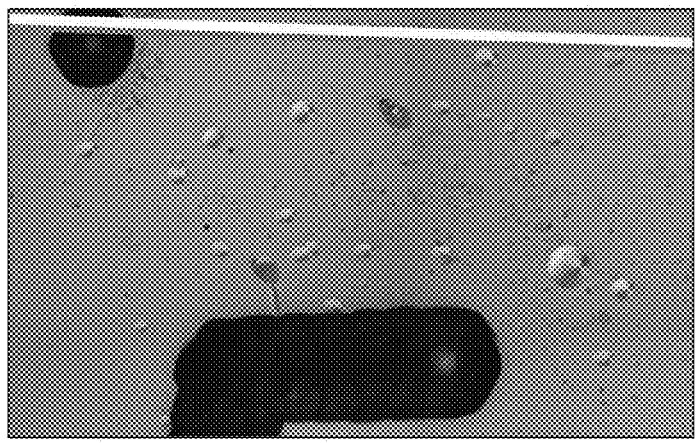

FIG. 6(a) is a photograph of transmitted polarized light taken by observing the substrate after washing with an XS-1 polarizing microscope made by Vision Psytec, Co., Ltd. As the observation conditions of the XS-1 polarizing microscope, the center wavelength CWL was set at 460 nm and the other conditions of the parallel light were the same as the Examples described above. FIG. 6(b) depicts an image produced by adjusting the obtained image (transmitted polarized light image) with Powerpoint (registered trademark) 2010 supplied by Microsoft (registered trademark) so that sharpness is +100% and contrast is −40%.

For this Example, etch pits were formed in the Si face of the n-type monocrystalline 4H—SiC substrate using KOH molten salt etching. After KOH molten salt etching, the n-type monocrystalline 4H—SiC substrate was sufficiently washed with purified water. After this, the etch pits observed using the ECLIPSE LV100D industrial microscope made by Nikon Inc. with the results depicted in FIG. 6(c).

By comparing the image (FIG. 6(a)) obtained by the XS-1 made by Vision Psytec, Co., Ltd., the image (FIG. 6(b)) in which optical distortions have been emphasized by image processing, and the image (FIG. 6(c)) of the etch pits, it can be understood that not only threading screw dislocations and threading edge dislocation but also optical distortions produced by the etch pits due to basal plane dislocations are observed by the XS-1 made by Vision Psytec, Co., Ltd.

A polarizing microscope used to the observation with a normal polarized light is limited to detecting micropipe defects when a monocrystalline 4H—SiC substrate has a thickness of 50 μm to 600 μm, and is unable to detect distortions caused by finer crystal defects. On the other hand, from the measurement results in this Example, it can be understood that by using parallel light 30 that satisfies the conditions given earlier, it is possible to non-destructively measure distortions caused by crystal defects that are finer than micropipes.

EXAMPLE 4

As the Example 4, a non-doped n-type monocrystalline GaN substrate manufactured by an ammonothermal method with a thickness of around 378 μm, a size that is 10 mm square, an epitaxy-ready Ga face, and a roughly finished N face was evaluated. The crystal orientation is c-plane (0001) and the off-angle is around 0.6°. The surface roughness Ra of the Ga face is below 0.5 nm and the surface roughness Ra of the N face is 20 nm to 30 nm. Since the bandgap of monocrystalline GaN is around 3.4 eV at room temperature, the conditions of the parallel light 30 were set the same as in the Example 1.

Figure 7:
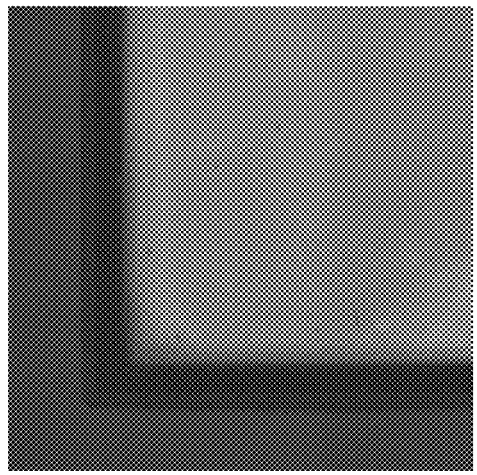
FIG. 7(a) is one example of imaging with an industrial microscope (white light) and FIG. 7(b) is one example of imaging using parallel light.
Figure 7:
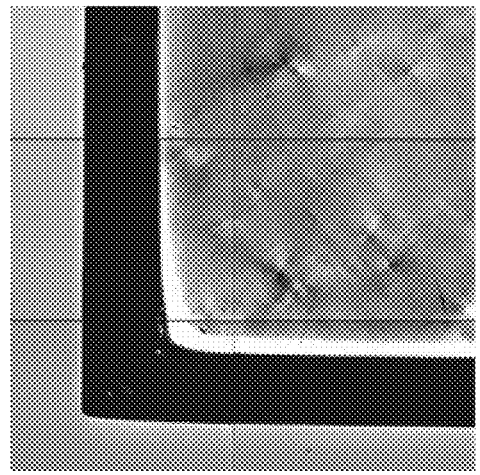

FIG. 7(a) depicts an image of transmitted simple polarized light produced by an ECLIPSE LV100D industrial microscope and FIG. 7(b) depicts an image of transmitted polarized light produced by the XS-1 polarizing microscope. With the ECLIPSE LV100D industrial microscope, white light was incident on the Ga face, but with the XS-1 polarizing microscope, the parallel light 30 was incident on the Ga face and was observed from the N face side. Although hardly any distortion can be observed in FIG. 7(a), in FIG. 7(b) a number of regions where the contrast between black and white is prominent can be observed. Accordingly, it is believed that in the region in which hardly anything is observed with the ECLIPSE LV100D industrial microscope that uses white light, it is possible to detect some type of crystal dislocations with the XS-1 polarizing microscope that irradiates the parallel light 30 onto the Ga face and makes observations from the N face side.

EXAMPLE 5

As the Example 5, a monocrystalline sapphire substrate that has a thickness of around 350 μm and a diameter of 50.8 mm and is mirror-finished on both surfaces was evaluated. The crystal orientation is c-plane (0001). Since monocrystalline sapphire is an insulating transparent oxide substrate, the conditions of the parallel light 30 were set as the same as in the Example 1.

Figure 8:
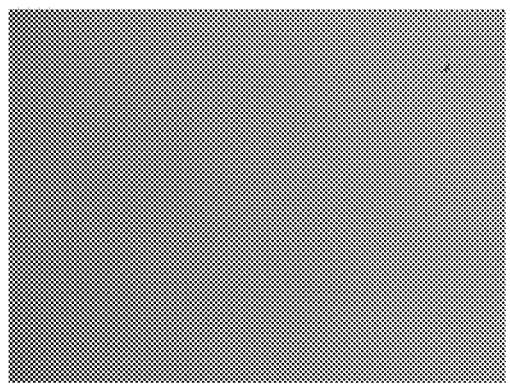
FIG. 8(a) is one example of imaging with an industrial microscope (white light) and FIG. 8(b) is one example of imaging using parallel light.
Figure 8:
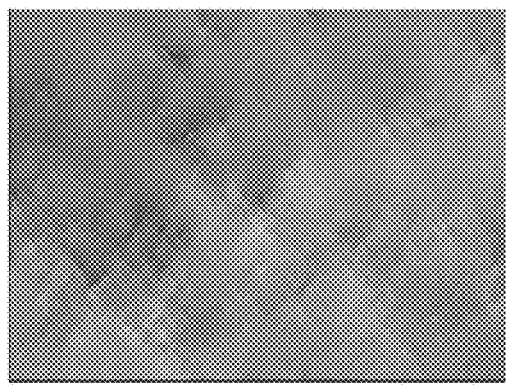

FIG. 8(a) depicts an image of transmitted simple polarized light produced by an ECLIPSE LV100D industrial microscope at an arbitrarily selected position in a central periphery of the substrate, and FIG. 8(b) depicts an image of transmitted polarized light at the same position produced by an XS-1 polarizing microscope. With the ECLIPSE LV100D industrial microscope, white light is incident on the preferential face and with the XS-1 polarizing microscope, the parallel light 30 is incident from the preferential face and is observed from the rear side. In FIG. 8(a), aside from adhering matter thought to be residue from washing, nothing can be seen, so that it can be understood that it is not possible to observe all optical distortions with the ECLIPSE LV100D industrial microscope that uses white light. On the other hand, in FIG. 8(b), a plurality of regions where the contrast between black and white is prominent are observed, and so that it can be understood that it is possible to detect some type of crystal dislocations with the XS-1 polarizing microscope that uses the parallel light 30.

EXAMPLE 6

As the Example 6, a polycrystalline silicon substrate that has a thickness of around 200 μm and a size of 156 mm and is subjected to CMP on both surfaces was evaluated. As the optical system, an optical system of the same configuration as the XS-1 polarizing microscope but assembled temporary like a barrack was used. As the observation conditions, an infrared LED light source with a center wavelength CWL 1550 nm was used, and the other conditions of the parallel light were set the same as the Examples described above. From the transmitted light, it was possible to observe crystal dislocation defects produced at the grain boundaries of polycrystalline silicon.

EXAMPLE 7

In the Example 7, evaluation was performed for an n-type monocrystalline silicon self-supporting epitaxial substrate produced by epitaxial growth of n-type monocrystalline silicon to a set thickness of 350 μm on the surface of a p-type monocrystalline silicon substrate that is 300 μm thick, removing the p-type monocrystalline silicon substrate by grinding and/or polishing, and then subjecting the rear surface to CMP to produce a residual thickness of 300 μm.

As the optical system, an optical system of the same configuration as the polarizing microscope XS-1 but assembled temporary was used. As the observation conditions, an infrared LED source with a center wavelength CWL of 1550 nm was used, and the other conditions of the parallel light were set the same as the Examples described above. Using the transmitted light, it was possible to observe misfit dislocation defects due to lattice mismatches between the p-type monocrystalline silicon and the n-type monocrystalline silicon.

Among monocrystalline silicon substrates, monocrystalline silicon substrates with a residual thickness of around 100 μm to 150 μm are used for solar cells and substrates that have been polished to around 60 μm for a withstand voltage of 600V are used as vertical power device such as IGBT (Insulated Gate Bipolar Transistors). For such 60 μm to 150 μm substrates, there may be increased transmittance, so that it was possible to observe distortion in such thin monocrystalline silicon substrates.

As described on the above, it was established that by using parallel light that is coherent quasi-monochromatic light and has been highly precisely collimated, it is possible to nondestructively test and evaluate crystal dislocations, such as threading screw dislocations, threading edge dislocations, and basal plane dislocations, and lattice distortion based on some kind of distortions in the atomic arrangement in all kinds of materials and substrates, in particular uniaxially polarized crystalline substrates, such as a monocrystalline 4H—SiC substrate using visible light or light in a wavelength range adjacent to visible light. Accordingly, it is possible to provide materials such as substrates that have been evaluated for the density, distribution, and the like of optical distortion using a polarizing microscope capable of supplying parallel light of predetermined conditions. When observing optical distortions due to crystal structure defects of uniaxially polarized crystal substrates such as a monocrystalline 4H—SiC substrate and a monocrystalline 6H—SiC substrate, it is preferable to set the center wavelength CWL of the light source at 310 nm to 460 nm. Also, when observing optical distortions due to crystal structure defects of a monocrystalline silicon substrate, an epitaxial monocrystalline silicon substrate, or a polycrystalline silicon substrate, it is preferable to set the center wavelength CWL of the light source at 1100 nm to 1600 nm, and more preferably at 1200 nm to 1550 nm.

With a conventional polarizing microscope, due to the optical characteristics that are a low degree of collimation and incoherence, transmitted polarized lights of a sample obtained with various angles interact each other and integrated. In addition, since a halogen lamp or the like that is a broadband light source with many wavelengths is used as the light source, the refractive index of the lens will vary between wavelengths, resulting in transmitted polarized light in various directions. Due to these factors, the spatial resolution for optical distortions inevitably falls.

With the testing method that uses polarized parallel light according to the present invention, by using high spatial coherence light that has limited wavelength (half width) and has been converted to collimated light, and passing such light in order through a polarizer, the substrate or the like to be observed, and an analyzer to detect the polarized light that has been transmitted, an effect is achieved whereby optical distortion based on crystal dislocations, such as threading screw dislocations, threading edge dislocations, and basal plane dislocations, caused by small displacements in an atomic arrangement can be easily detected using a polarizing microscope.

This testing (inspecting, evaluating) method is not limited to uniaxially polarized crystal substrates such as the monocrystalline 4H—SiC substrates and monocrystalline 6H—SiC substrates that are explained in the Examples given above, and can also be applied to a wide variety of substrates including substrates produced by epitaxial growth on a uniaxially polarized crystal substrate, wide bandgap semiconductor substrates and substrates produced by epitaxial growth on the same, other semiconductor monocrystalline substrates and substrates produced by epitaxial growth on the same, mineral substrates, monocrystalline silicon substrates, substrates produced by epitaxial growth on monocrystalline silicon substrates, polycrystalline silicon, glass substrates, plastic substrates, and plastic film substrates. Wide bandgap semiconductor substrates include monocrystalline GaN, monocrystalline $Ga_2O_3$, monocrystalline AlN, monocrystalline diamond and the like. This testing method is also applicable to the substrates that have a thin film of metal, semiconductor, oxide, an organic material or an inorganic compound formed on a surface on the substrate described above, and the thin film may be a heteroepitaxially grown film.

As one example, according to the present invention, it is possible to detect optical distortions (birefringence) due to crystal structure defects in uniaxially polarized crystal substrates, such as a monocrystalline 4H—SiC substrate or a monocrystalline 6H—SiC substrate, or an epitaxially grown substrate, in particular, it is possible to detect optical distortions (birefringence) for any of micropipe defects, threading screw dislocations, threading edge dislocations, basal plane dislocations, stacking faults, inclusions, and other processing or machining damage with visible light or light in a region near visible light. In particular, optical distortions based on crystal dislocations such as threading screw dislocations, threading edge dislocations, and basal plane dislocations, and other lattice distortions caused by displacements in the atomic arrangement of a crystalline substrate are observed with an optical microscope using parallel light that satisfies the conditions of the present invention and/or the optical microscope images are photographed, which makes it possible to observe crystal dislocations as optical distortions, to evaluate the density, distribution, and the like of crystal dislocations and the like as optical distortions (birefringence), and/or to evaluate photoelasticity. This means that it is possible to provide a method including testing or inspecting of substrates easily and at low cost compared to methods such as synchrotron X-ray topography and photoluminescence that were conventionally used for these purposes.

The invention claimed is:

1. A method comprising:
    illuminating a substrate with polarized parallel light: and
    evaluating a crystal quality of at least a part of the substrate from an image obtained by light transmitted through or reflected by the substrate,
    wherein a half width HW, a divergence angle DA, and a center wavelength CWL of the parallel light satisfy conditions given below $3 \leq HW \leq 100$ $0.1 \leq DA \leq 5$ $250 \leq CWL \leq 1600$ where the center wavelength CWL and the half width HW are expressed in units of nm and the divergence angle DA is expressed in units of mrad.

2. The method according to claim 1, wherein the half width HW satisfies a condition given below $3 < HW < 60$.

3. The method according to claim 1, wherein the divergence angle DA satisfies a condition given below $0.1 < DA < 3$.

4. The method according to claim 1, wherein the center wavelength CWL satisfies a condition given below $300 < CWL < 500$.

5. The method according to claim 1, wherein the center wavelength CWL satisfies a condition given below $1100 < CWL < 1600$.

6. The method according to claim 1,
    wherein the evaluating includes evaluation with a crossed Nicol and an extinction ratio ER of a polarizer and an analyzer that face one another with the substrate in between satisfies a condition given below $10^{-4} < ER < 10^{-2}$.

7. The method according to claim 1,
    wherein the evaluating includes changing a focal depth.

8. The method according to claim 1,
    wherein the evaluating includes evaluating lattice distortions based on displacements in an atomic arrangement.

9. The method according to claim 8,
    wherein the lattice distortions based on the displacements in the atomic arrangement include threading screw dislocations, threading edge dislocations, basal plane dislocations, stacking faults, inclusions, and processing damages.

10. The method according to claim 1,
    wherein the evaluating includes evaluating photoelasticity.

11. The method according to claim 1,
    wherein the substrate is any of a semiconductor substrate, a monocrystalline semiconductor substrate and monocrystalline semiconductor substrate with epitaxial growth, a mineral substrate, a glass substrate, a plastic substrate, or a plastic film substrate.

12. The method according to claim 11,
    wherein the monocrystalline semiconductor substrate includes at least one of:
    a uniaxially polarity crystalline substrate including a monocrystalline 4H—SiC substrate or a monocrystalline 6H—SiC substrate;
    a wide bandgap semiconductor substrate including at least one of monocrystalline GaN, monocrystalline $Ga_2O_3$, monocrystalline AlN and monocrystalline diamond;
    a monocrystalline substrate of a transparent oxide such as monocrystalline sapphire;
    a monocrystalline silicon substrate; and
    a monocrystalline silicon substrate with epitaxial growth.

13. The method according to claim 11,
    wherein the monocrystalline semiconductor substrate is a uniaxially polarized crystalline substrate that includes a monocrystalline 4H—SiC substrate or a monocrystalline 6H—SiC substrate and a thickness t thereof satisfies a condition given below $50 \leq t \leq 600$ where the thickness t is expressed in units of μm.

14. The method according to claim 1,
    wherein a surface roughness Ra1 of a front surface side of the substrate satisfies a condition given below $0.001 \leq Ra1 \leq 30$ where the surface roughness Ra1 is expressed in units of nm.

15. The method according to claim 14,
    wherein the surface roughness Ra1 of the front surface side of the substrate satisfies a condition given below $0.001 \leq Ra1 \leq 1$.

16. The method according to claim 1,
    wherein a surface roughness Ra2 of a rear surface side of the substrate satisfies a condition given below $0.001 \leq Ra2 \leq 30$ where the surface roughness Ra2 is expressed in units of nm.

17. The method according to claim 16,
    wherein the surface roughness Ra2 of the rear surface side of the substrate satisfies a condition given below $0.001 \leq Ra2 \leq 1$.

18. The method according to claim 1,
    further comprising manufacturing a product that uses a substrate selected by the evaluating.

19. The method according to claim 1,
    further comprising subjecting a region of the substrate determined by the evaluating to a treatment.

* * * * *